US009358263B2

(12) United States Patent
Millikin et al.

(10) Patent No.: US 9,358,263 B2
(45) Date of Patent: Jun. 7, 2016

(54) PERSONAL CARE COMPOSITION COMPRISING BOTANICAL EXTRACT

(75) Inventors: Cheri Lynn Millikin, West Chester, OH (US); Laura Jackson Goodman, Hamilton, OH (US); Donald Lynn Bissett, Hamilton, OH (US); Larry Richard Robinson, Loveland, OH (US); Rosemarie Osborne, Oxford, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1407 days.

(21) Appl. No.: 12/039,409

(22) Filed: Feb. 28, 2008

(65) Prior Publication Data

US 2008/0206373 A1 Aug. 28, 2008

Related U.S. Application Data

(60) Provisional application No. 60/904,123, filed on Feb. 28, 2007.

(51) Int. Cl.
*A61K 36/00* (2006.01)
*A61K 36/60* (2006.01)
*A61K 8/97* (2006.01)
*A61K 36/82* (2006.01)
*A61Q 19/02* (2006.01)
*A61Q 19/08* (2006.01)

(52) U.S. Cl.
CPC . *A61K 36/60* (2013.01); *A61K 8/97* (2013.01); *A61K 36/82* (2013.01); *A61Q 19/02* (2013.01); *A61Q 19/08* (2013.01)

(58) Field of Classification Search
None
See application file for complete search history.

(56) References Cited

U.S. PATENT DOCUMENTS

| | | | | |
|---|---|---|---|---|
| 2,898,269 | A * | 8/1959 | Felletschin | 514/783 |
| 3,755,560 | A | 8/1973 | Dickert et al. | |
| 4,421,769 | A | 12/1983 | Dixon et al. | |
| 4,496,536 | A * | 1/1985 | Moller et al. | 424/70.8 |
| 5,053,222 | A * | 10/1991 | Takasu et al. | 514/106 |
| 5,102,655 | A * | 4/1992 | Yoshihara et al. | 424/62 |
| 5,314,873 | A * | 5/1994 | Tomita et al. | 514/21 |
| 5,879,665 | A | 3/1999 | Fuller | |
| 6,153,177 | A * | 11/2000 | Bartolone et al. | 424/62 |
| 6,159,485 | A | 12/2000 | Yu et al. | |
| 6,348,200 | B1 * | 2/2002 | Nakajima et al. | 424/401 |
| 7,241,606 | B2 * | 7/2007 | Kubota et al. | 435/193 |
| 7,507,424 | B2 | 3/2009 | Mitra et al. | |
| 2002/0168329 | A1 * | 11/2002 | Kini et al. | 424/70.22 |
| 2003/0054054 | A1 | 3/2003 | Bassa | |
| 2003/0091620 | A1 * | 5/2003 | Fikstad et al. | 424/449 |
| 2003/0133960 | A1 * | 7/2003 | Duranton et al. | 424/401 |
| 2004/0071803 | A1 | 4/2004 | Murthy et al. | |
| 2004/0076650 | A1 * | 4/2004 | Blin et al. | 424/401 |
| 2006/0018867 | A1 * | 1/2006 | Kawasaki et al. | 424/70.122 |
| 2006/0134033 | A1 * | 6/2006 | Cassin | 424/63 |
| 2006/0134155 | A1 * | 6/2006 | Dryer et al. | 424/401 |
| 2006/0142382 | A1 * | 6/2006 | Morimoto et al. | 514/474 |
| 2006/0275332 | A1 * | 12/2006 | Agarwal et al. | 424/401 |
| 2008/0025932 | A1 | 1/2008 | Bissett et al. | |
| 2008/0214669 | A1 * | 9/2008 | Dayan et al. | 514/570 |
| 2009/0143458 | A1 * | 6/2009 | Jensen et al. | 514/423 |

FOREIGN PATENT DOCUMENTS

| | | | |
|---|---|---|---|
| JP | 57064606 | * | 4/1982 |
| JP | 58170707 | * | 10/1983 |
| JP | 61155318 | * | 7/1986 |
| JP | 03193727 | * | 8/1991 |
| JP | 08183724 | * | 7/1996 |
| JP | 08183725 | * | 7/1996 |
| JP | 2004/359571 | | 12/2004 |
| KR | 9504694 | * | 5/1995 |
| WO | WO 2005/115090 A3 | | 4/2006 |

OTHER PUBLICATIONS

ChemNet website document entitled 'Hexyldecanol'. Downloaded Mar. 10, 2011. 1-page. Downloaded Mar. 10, 2011. Obtained from http://davidjia.en.chemnet.com/suppliers/product/1203110/Hexyldecanol.html.*
U.S. Appl. No. 61/381,748, filed Sep. 2, 2010, Swanson, et al.
U.S. Appl. No. 61/445,487, filed Feb. 22, 2011, Swanson.
U.S. Appl. No. 61/445,494, filed Feb. 22, 2011, Swanson.
Das Mohapatra, et al., "Production of tannase through submerged fermentation of tannin-containing plant extracts by Bacillus Licheniformis KBR6," Polish Journal of Microbiology, vol. 55, No. 4, 2006, pp. 297-301.
Database WPI Week 200169, Thomson Scientific, London, GB, AN 2001-605339.
Database WPI Week 200504, Thomson Scientific, London, GB, AN 2005-035832.
Gabhe, et al. "Evaluation of the immunomodulatory activity of the methanol extract of *Ficus benghalensis* roots in rats," Indian Journal of Pharmacology, vol. 38, No. 4, 2006, pp. 271-257, internet http://www.i jp-online.com/text.asp?200.
International Search Report, PCT/IB2008/050705, dated Feb. 28, 2007.
Parekh, et al., "Efficacy of aqueous and methanol extracts of some medicinal plants for potential antibacterial activity," Turk J. Biol., vol. 29, 2005, pp. 203-210.
U.S. Appl. No. 61/381,748, filed Sep. 2, 2010, Swanson.

* cited by examiner

*Primary Examiner* — Chris R Tate
(74) *Attorney, Agent, or Firm* — John G. Powell

(57) ABSTRACT

Personal care composition comprising at least one extract selected from the group consisting of extracts of *Terminalia bellerica, Butea monosperma, Mallotus philippinensis, Anogeissus latifolia, Innula racemosa, Ficus benghalensis, Nerium indicum, Psoralea corylifolia, Acacia catechu, Abies pindrow, Cedrus deodara, Emblica officinalis, Moringa oleifera, Glycyrrhiza glabra*, and mixtures thereof, and a dermatologically acceptable carrier. Additionally or alternatively, the composition may comprise 2-hexyldecanol.

14 Claims, No Drawings

PERSONAL CARE COMPOSITION COMPRISING BOTANICAL EXTRACT

CROSS REFERENCE TO RELATED APPLICATION

This application claims the benefit of U.S. Provisional Application No. 60/904,123 filed Feb. 28, 2007.

FIELD OF THE INVENTION

The present invention relates to personal care compositions comprising at least one extract and/or skin care active useful for regulating the condition of mammalian keratinous tissue. The present invention further relates to methods of use of the personal care composition, a kit, an article of commerce, and a method of marketing the personal care composition described herein.

BACKGROUND OF THE INVENTION

A number of personal care products, which are directed toward improving the health and physical appearance of keratinous tissues such as the skin, hair, and nails, currently are available to consumers. There exists a continuing need, however, to regulate the condition of keratinous tissue by delaying, minimizing or even eliminating skin wrinkling and histological changes typically associated with the aging of skin or environmental damage to human skin. In addition, there exists a need for cosmetic agents to prevent, retard, and/or treat uneven skin tone by acting as a skin lightening or pigmentation reduction cosmetic agent.

SUMMARY OF THE INVENTION

The present invention meets the aforementioned needs. Applicants believe that personal care compositions comprising one or more botanical extracts and/or skin care actives described herein may be used to provide prophylactic as well as therapeutic regulation of keratinous tissue conditions. The compositions of the present invention may be particularly useful for improving skin tone and texture, e.g., lightening skin, reducing the appearance of hyperpigmentation, and reducing the appearance of wrinkles.

The following describe some non-limiting embodiments of the present invention.

According to a first embodiment of the present invention, a personal care composition is provided comprising *Ficus benghalensis* and a dermatologically acceptable carrier.

According to yet another embodiment of the present invention, a method of regulating the condition of mammalian keratinous tissue is provided comprising the step of topically applying to the keratinous tissue of a mammal needing such treatment a personal care composition according to the first embodiment.

According to yet another embodiment of the present invention, an article of commerce is provided comprising a personal care composition according to the first embodiment; packaging for the personal care composition and/or a communication pertaining to the personal care composition. The communication may comprise images comparing the appearance of a person prior to use of the composition to the appearance of the same person after use of the composition. Additionally or alternatively, the communication may comprise indicia and/or an image which communicates that the personal care composition can be used in conjunction with an energy delivery device for regulating the condition of mammalian keratinous tissue.

DETAILED DESCRIPTION OF THE INVENTION

The compositions of the present invention may be used in a variety of personal care products, non-limiting examples of which include moisturizers, conditioners, cleansers, sunscreens, anti-aging compounds, cosmetics (including lipstick, foundation, rouges, and/or mascara), and combinations thereof. The composition may be in a variety of forms, including but not limited to an emulsion, lotion, milk, liquid, solid, cream, gel, mousse, ointment, paste, serum, stick, spray, tonic, aerosol, foam, pencil, etc. The compositions of the present invention also may be in the form of shave prep products, including, for example, gels, foams, lotions, and creams; and include both aerosols and non-aerosols versions. In one embodiment, the composition is in a form suitable for use with an implement, for example, such as a swab and/or a pen.

In all embodiments of the present invention, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. All measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

"Personal care composition," as used herein, means compositions suitable for topical application on mammalian keratinous tissue.

"Skin care actives," or "actives," as used herein, means compounds that, when applied to the skin, provide a benefit or improvement to the skin. It is to be understood that skin care actives are useful not only for application to skin, but also to hair, nails and other mammalian keratinous tissue.

"Keratinous tissue," as used herein, refers to keratin-containing layers disposed as the outermost protective covering of mammals which includes, but is not limited to, skin, hair, nails, cuticles, etc.

"Dermatologically acceptable," as used herein, means that the compositions or components described are suitable for use in contact with human keratinous tissue without undue toxicity, incompatibility, instability, allergic response, and the like.

"Effective amount" as used herein means an amount of a compound or composition sufficient to significantly induce a positive benefit, preferably a positive keratinous tissue appearance or feel benefit, including independently or in combination the benefits disclosed herein, but low enough to avoid serious side effects (i.e., to provide a reasonable benefit to risk ratio, within the scope of sound judgment of the skilled artisan).

"Delivery enhancement device," as used herein, means any device that increases the amount of active ingredient applied to and/or into the skin relative to the amount of active ingredient that is delivered without using the device.

"Regulating the condition of mammalian keratinous tissue," as used herein, means improving appearance and/or feel of keratinous tissue, for example, by providing a smoother appearance and/or feel of skin.

"Improving skin condition" means effecting a visually and/or tactilely perceptible positive change, or benefit, in skin appearance and feel. Benefits that may be provided include, but are not limited to, one or more of the following: Reducing the appearance of wrinkles and coarse deep lines, fine lines, crevices, bumps, and large pores; thickening of keratinous tissue (e.g., building the epidermis and/or dermis and/or sub-dermal layers of the skin, and where applicable the keratinous layers of the nail and hair shaft, to reduce skin, hair, or nail atrophy); increasing the convolution of the dermal-epidermal border (also known as the rete ridges); skin lightening; preventing loss of skin or hair elasticity, for example, due to loss, damage and/or inactivation of functional skin elastin, resulting in such conditions as elastosis, sagging, loss of skin or hair recoil from deformation; reduction in cellulite; change in coloration to the skin, hair, or nails, for example, under-eye circles, blotchiness (e.g., uneven red coloration due to, for example, rosacea), sallowness, discoloration caused by hyperpigmentation, etc.

"Signs of skin aging," as used herein, include but are not limited to, all outward visibly and tactilely perceptible manifestations, as well as any macro- or microeffects, due to keratinous tissue aging. These signs may result from processes which include, but are not limited to, the development of textural discontinuities such as wrinkles and coarse deep wrinkles, fine lines, skin lines, crevices, bumps, large pores, unevenness or roughness; loss of skin elasticity; discoloration (including undereye circles); blotchiness; sallowness; hyperpigmented skin regions such as age spots and freckles; keratoses; abnormal differentiation; hyperkeratinization; elastosis; collagen breakdown, and other histological changes in the stratum corneum, dermis, epidermis, vascular system (e.g., telangiectasia or spider vessels), and underlying tissues (e.g., fat and/or muscle), especially those proximate to the skin.

"Hyperpigmentation," as used herein, refers to an area of skin wherein the pigmentation is greater than that of an adjacent area of skin (e.g., a pigment spot, an age spot, and the like).

"Desquamation, exfoliation, and/or turnover," as used herein, mean the removal of the upper layers of the stratum corneum (comprising the horny layers).

"Sallowness," as used herein means the pale color, yellow color or the like condition of skin that occurs as a result of a loss of, damage to, alterations to, and/or abnormalities in skin components such that they become colored (e.g., yellow in color) due to processes such as protein glycation and accumulation of lipofuscin or in the decrease in peripheral blood flow that typically accompanies skin aging.

"Derivatives," as used herein, includes but is not limited to, amide, ether, ester, amino, carboxyl, acetyl, and/or alcohol derivatives of a given compound.

"Isomers," as used herein, is understood to include D-isomers, L-isomers, and/or DL-isomers of a given compound.

"Salts," as used herein, includes but is not limited to sodium, potassium, calcium, ammonium, manganese, copper, and/or magnesium salts of a given compound.

"Extract," as used herein, means material that may be obtained by the following procedure: Place the indicated portion of dried plant material (stem, bark, leaves, etc.) in a conical glass percolator. Add the indicated percentage of extraction solvent in a w/w ratio of 1 part plant material to 2 parts extraction solvent. When the indicated percentage of extraction solvent is less than 100%, the remaining solvent is water (e.g., 95% ethanol with 5% water, 50% ethanol with 50% water, etc.). Allow the extraction to proceed for about 16 to about 24 hours. Collect the percolate, and repeat the above process until the resulting percolate is substantially free from plant additional extract. Combine the percolates, evaporate to dryness under reduced pressure, and store the resulting extract under nitrogen at less than 4 degrees Celsius.

"Further fractionation," as used herein, means a fraction of an extract that may be obtained by the following procedure: Combine from about 3 g to about 5 g) with silica gel (200-400 mesh) to produce a uniform slurry. Charge the slurry in a 5 cm silica gel band (200-400 mesh size, approximate weight 25 g) in a 150 ml capacity column (3.6 cm dia) on a flash chromatograph. Elute with the indicated solvent or solvent combinations. For each solvent or solvent system, collect 2 to 4 fractions of 75-150 mL each. Remove the solvent from the fraction by evaporation under pressure. Store the resulting fractions were stored in the dark at a temperature below 10° C.

"Early fraction," as used herein, means the first collected fraction obtained during further fractionation.

"Late fraction," as used herein, means the last collected fraction obtained during further fractionation.

I. Personal Care Composition

The composition of the present invention may comprise from about 0.01% to about 10%, alternatively from about 0.1% to about 7%, alternatively from about 0.1% to about 5%, and alternatively from about 0.5% to about 3%, of one or more of the following extracts, fractions thereof, and salts, isomers, and/or derivatives thereof:

1. *Terminalia bellerica* stem bark extract (ref. extract 1): An extract of stem bark of the plant *Terminalia bellerica* derived from a 95% ethanol extraction, which is believed to be useful as an anti oxidant, an activator of glutathione, an upregulator of ARE and ARE-allosteric, and a nitric oxide scavenger.

2. *Butea monosperma* stem extract (ref. extract 3): An extract of the stem of the plant *Butea monosperma* derived from a 95% ethanol extraction, which is believed to be useful as an anti oxidant, an activator of glutathione, an upregulator of ARE and ARE-allosteric, and a nitric oxide scavenger.

3. *Butea monosperma* stem extract (ref. extract 4): An extract of the stem of the plant *Butea monosperma* derived from a 95% ethanol extraction and further fractionated on a silica gel column and eluted with 50% ethanol, which is believed to be useful as an inhibitor of tyrosinase, an anti oxidant, an inhibitor of trypsin, an upregulator of ARE-allosteric, and a nitric oxide scavenger.

4. *Butea monosperma* stem bark extract (ref. extract 5): An extract of the stem bark of the plant *Butea monosperma* derived from a 95% ethanol extraction and further fractionated on a silica gel column and eluted with 50% ethanol, which is believed to be useful as an inhibitor of tyrosinase, an anti oxidant, an inhibitor of trypsin, an inhibitor of cAMP, an activator of glutathione, an upregulator of ARE-allosteric, inhibitor of lipogenesis, and a nitric oxide scavenger.

5. *Mallotus philippinensis* stem bark extract (ref extract 6): An extract of the stem bark of the plant *Mallotus philippinensis* derived from a 50% ethanol extraction, which is believed to be useful as an inhibitor of trypsin, an anti oxidant, an inhibitor of lipogenesis, and a nitric oxide scavenger.

6. *Anogeissus latifolia* stem and leaf extract (ref extract 7): An extract of the stem and leaves of the plant *Anogeissus latifolia* derived from a 95% ethanol extraction, which is believed to be useful as an anti oxidant, an inhibitor of COX 2, inhibitor of cAMP, activator of glutathione, and a nitric oxide scavenger.
7. *Innula racemosa* root extract (ref extract 8): An extract of the root of the plant *Innula racemosa* derived from a 95% ethanol extraction, which is believed to be as an upregulator of ARE-allosteric, an inhibitor of lipogenesis, and an inhibitor of cAMP.
8. *Ficus benghalensis* stem extract (ref. extract 9): An extract of the stem of the plant *Ficus benghalensis* derived from a 95% ethanol extraction, further fractioned on a silica gel column and found in the early fraction upon elution with 95% ethanol, which is believed to be useful as an anti oxidant, an inhibitor of trypsin, an upregulator of ARE-allosteric, an activator of glutathione, an inhibitor of cAMP, and a nitric oxide scavenger.
9. *Ficus benghalensis* stem extract (ref. extract 10): An extract of the stem of the plant *Ficus benghalensis* derived from a 95% ethanol extraction of the stem, further fractioned on a silica gel column and found in the late fraction upon elution with 95% ethanol, which is believed to be useful as an anti oxidant, an inhibitor of trypsin, an inhibitor of tyrosinase, upregulator of ARE-allosteric, inhibitor of lipogenesis, and a nitric oxide scavenger.
10. *Ficus benghalensis* stem extract (ref. extract 11): An extract of the stem of the plant *Ficus benghalensis* derived from a 95% ethanol extraction of the stem, further fractioned on a silica gel column and eluted with 50% ethanol, which is believed to be useful as an anti oxidant, an inhibitor of trypsin, an inhibitor of tyrosinase, an activator of glutathione, an upregulator of ARE and ARE-allosteric, an inhibitor of lipogenesis, and a nitric oxide scavenger.
11. *Ficus benghalensis* leaf extract (ref. extract 12): An extract of the leaves of the plant *Ficus benghalensis* derived from a 95% ethanol extraction, which is believed to be useful as an anti oxidant, an inhibitor of trypsin, an inhibitor of tyrosinase, activator of glutathione, inhibitor of cAMP, upregulator of ARE and ARE-allosteric, inhibitor of lipogenesis, and a nitric oxide scavenger.
12. *Ficus benghalensis* leaf extract (ref extract 14): An extract of the leaves of the plant *Ficus benghalensis* derived from a 50% ethanol extraction, which is believed to be useful as an anti oxidant, an inhibitor of trypsin, an inhibitor of tyrosinase, an activator of glutathione, an upregulator of ARE, and a nitric oxide scavenger.
13. *Ficus benghalensis* stem bark extract (ref extract 17): An extract of the stem bark of the plant *Ficus benghalensis* derived from a 50% ethanol extraction, further fractionated on a silica gel column and eluted with 20% ethanol, which is believed to be useful as an anti oxidant, an inhibitor of trypsin, an activator of glutathione, an inhibitor of lipogenesis, and a nitric oxide scavenger.
14. *Nerium indicum* stem and leaf extract (ref extract 19): An extract of the stem and leaves of the plant *Nerium indicum* derived from a 95% ethanol extraction, which is believed to be useful as an inhibitor of trypsin, an upregulator of ARE, an inhibitor of lipogenesis, and a nitric oxide scavenger.
15. *Psoralea corylifolia* seed extract (ref. extract 21): An extract of the seeds of the plant *Psoralea corylifolia* derived from a 95% ethanol extraction, further fractionated on a silica gel column and eluted with 100% ethyl acetate, which is believed to be useful as an anti oxidant, an inhibitor of trypsin, an inhibitor of tyrosinase, an upregulator of ARE, an inhibitor of lipogenesis, and a nitric oxide scavenger.
16. *Acacia catechu* fruit extract (ref. extract 22): An extract of the fruit of the plant *Acacia catechu* derived from a 95% ethanol extraction, which is believed to be useful as an anti oxidant, an inhibitor of trypsin, an inhibitor of tyrosinase, an activator of glutathione, an inhibitor of lipogenesis, an inhibitor of cAMP, and a nitric oxide scavenger.
17. *Acacia catechu* fruit extract (ref. extract 24): An extract of the fruit of the plant *Acacia catechu* derived from a 95% ethanol extraction of the fruit, and further fractionated on a silica gel column and eluted with 95% ethanol, which is believed to be useful as an anti oxidant, an inhibitor of trypsin, an inhibitor of tyrosinase, an activator of glutathione, an inhibitor of lipogenesis, an inhibitor of cAMP, and a nitric oxide scavenger.
18. *Acacia catechu* fruit extract (ref. extract 25): An extract of the fruit of the plant *Acacia catechu* derived from a 95% ethanol extraction, further fractionated on a silica gel column and eluted with 50% ethanol, which is believed to be useful as an anti oxidant, an inhibitor of trypsin, an inhibitor of tyrosinase, an activator of glutathione, an inhibitor of lipogenesis, an inhibitor of cAMP, and a nitric oxide scavenger.
19. *Acacia catechu* fruit extract (ref. extract 26): An extract of the fruit of the plant *Acacia catechu* derived from a 50% ethanol extraction of the fruit, and further fractionated on a silica gel column and eluted with 95% ethanol, has been identified as an anti oxidant, an inhibitor of trypsin, an inhibitor of tyrosinase, an inhibitor of COX 2, an activator of glutathione, an inhibitor of lipogenesis, and a nitric oxide scavenger.
20. *Abies pindrow* stem bark extract (ref. extract 31): An extract of the stem bark of the plant *Abies pindrow* derived from a 50% ethanol extraction, which is believed to be useful as an anti oxidant, an inhibitor of trypsin, an inhibitor of COX 2, an activator of glutathione, an inhibitor of lipogenesis, an inhibitor of cAMP, and a nitric oxide scavenger.
21. *Abies pindrow* stem bark extract (ref. extract 32): An extract of the stem bark of the plant *Abies pindrow* derived from a 50% ethanol extraction, and further fractionated on a silica gel column and eluted with 95% ethanol, which is believed to be useful as an anti oxidant, an inhibitor of trypsin, an inhibitor of tyrosinase, an inhibitor of COX 2, an activator of glutathione, an inhibitor of lipogenesis, an upregulator of ARE, and a nitric oxide scavenger.
22. *Cedrus deodara* stem bark extract (ref. extract 33): An extract of the stem bark of the plant *Cedrus deodara* derived from a 50% ethanol extraction, which is believed to be useful as an anti oxidant, an inhibitor of trypsin, an inhibitor of tyrosinase, an activator of glutathione, an inhibitor of lipogenesis, an inhibitor of cAMP, and a nitric oxide scavenger.
23. *Cedrus deodara* stem bark extract (ref. extract 34): An extract of the stem bark of the plant *Cedrus deodara* derived from a 50% ethanol extraction, and further fractionated on a silica gel column and found in the early fraction upon elution with 95% ethanol, which is believed to be useful as an anti oxidant, an inhibitor of trypsin, an inhibitor of tyrosinase, an activator of glutathione, an inhibitor of lipogenesis, an inhibitor of cAMP, an upregulator of ARE, and a nitric oxide scavenger.

24. *Cedrus deodara* stem bark extract (ref. extract 35): An extract of the stem bark of the plant *Cedrus deodara* derived from a 50% ethanol extraction, and found in the late fraction upon further fractionation on a silica gel column and elution with 95% ethanol, which is believed to be useful as an anti oxidant, an inhibitor of trypsin, an inhibitor of tyrosinase, an activator of glutathione, an inhibitor of lipogenesis, an inhibitor of cAMP, an upregulator of ARE, and a nitric oxide scavenger.

25. *Cedrus deodara* stem bark extract (ref. extract 36): An extract of the stem bark of the plant *Cedrus deodara* derived from a 50% ethanol extraction, and further fractionated on a silica gel column and eluted with 20% ethanol, which is believed to be useful as an anti oxidant, an inhibitor of lipogenesis, and an inhibitor of trypsin.

26. *Emblica officinalis* stem bark extract (ref. extract 38): An extract of the stem bark of the plant *Emblica officinalis* derived from a 95% ethanol extraction, and found in the early fraction upon further fractionation on a silica gel column with 95% ethanol, which is believed to be useful as an anti oxidant, an inhibitor of COX 2, an activator of glutathione, an inhibitor of lipogenesis, an upregulator of ARE and ARE-allosteric, and a nitric oxide scavenger.

27. *Emblica officinalis* stem bark extract (ref. extract 39): An extract of the stem bark of the plant *Emblica officinalis* derived from a 95% ethanol extraction, and found in the late fraction upon further fractionation on a silica gel column with 95% ethanol, which is believed to be useful as an anti oxidant, an inhibitor of trypsin, an inhibitor of COX 2, an activator of glutathione, an inhibitor of lipogenesis, an upregulator of ARE and ARE-allosteric, and a nitric oxide scavenger 28. *Emblica officinalis* stem bark extract (ref. extract 40): An extract of the stem bark of the plant *Emblica officinalis* derived from a 50% ethanol extraction, which is believed to be useful as an anti oxidant, an inhibitor of trypsin, an inhibitor of COX 2, an inhibitor of tyrosinase, an activator of glutathione, an inhibitor of lipogenesis, an inhibitor of cAMP, an upregulator of ARE, and a nitric oxide scavenger.

29. *Emblica officinalis* stem bark extract (ref. extract 41): An extract of the stem bark of the plant *Emblica officinalis* derived from a 50% ethanol extraction, and further fractionated on a silica gel column and eluted with 95% ethanol, which is believed to be useful as an anti oxidant, an inhibitor of trypsin, an inhibitor of COX 2, and a nitric oxide scavenger.

30. *Emblica officinalis* stem bark extract (ref. extract 42): An extract of the stem bark of the plant *Emblica officinalis* derived from a 50% ethanol extraction, and further fractionated on a silica gel column and eluted with 20% ethanol, which is believed to be useful as anti oxidant, an inhibitor of trypsin, an inhibitor of tyrosinase, an inhibitor of COX 2, an activator of glutathione reductase, an activator of total glutathione, an upregulator of ARE-allosteric, an inhibitor of lipogenesis, and a nitric oxide scavenger.

31. *Emblica officinalis* stem bark extract (ref. extract 44): An extract of the stem bark of the plant *Emblica officinalis* derived from a 100% water extraction, and further fractionated on a silica gel column and eluted with 66% ethanol, which is believed to be useful as an anti oxidant, an inhibitor of trypsin, an inhibitor of tyrosinase, an activator of glutathione, an inhibitor of cAMP, an upregulator of ARE and ARE-allosteric, an inhibitor of lipogenesis, an inhibitor of COX 2, and a nitric oxide scavenger.

32. *Emblica officinalis* stem bark extract (ref. extract 45): An extract of the stem bark of the plant *Emblica officinalis* derived from a 100% water extraction, and further fractionated on a silica gel column and eluted with 66% ethanol, which is believed to be useful as an anti oxidant, an inhibitor of trypsin, an inhibitor of COX 2, an inhibitor of cAMP, an upregulator of ARE and ARE-allosteric, an inhibitor of lipogenesis, and a nitric oxide scavenger.

33. *Moringa oleifera* leaf extract (ref. extract 46): An extract of the leaves of the plant *Moringa oleifera* derived from a 50% ethanol extraction, and further fractionated on a silica gel column and eluted with 20% ethanol, which is believed to be useful as an activator of glutathione reductase and an activator of epidermal hyaluronic acid.

34. *Glycyrrhiza glabra* root extract (ref. extract 49): An extract of the roots of the plant *Glycyrrhiza glabra* derived from a 95% ethanol extraction, and further fractionated on a silica gel column and eluted with 50% ethanol, which is believed to be useful as an anti oxidant, an activator of glutathione, and an inhibitor of tyrosinase.

35. *Glycyrrhiza glabra* root extract (ref. extract 50): An extract of the root of the plant *Glycyrrhiza glabra* derived from a 95% ethanol extraction, and further fractionated on a silica gel column and eluted with 50% ethanol, which is believed to be useful as an inhibitor of tyrosinase, an activator of glutathione, an upregulator of ARE-allosteric, and a nitric oxide scavenger.

36. *Glycyrrhiza glabra* root extract (ref. extract 51): An extract of the roots of the plant *Glycyrrhiza glabra* derived from a 95% ethanol extraction, and further fractionated on a silica gel column and eluted with 50% ethanol, has been identified as an activator of glutathione.

Additionally or alternatively, the composition of the present invention may comprise from about 0.01% to about 10%, alternatively from about 0.05% to about 5%, and alternatively from about 0.1% to about 1%, of 2-hexyldecanol (CAS 2425-77-6), believed to be useful as an inhibitor of melanin synthesis. The 2-hexyldecanol of the present invention is commercially available from Sigma-Aldrich, Milwaukee, Wis.

Additional Skin Care Actives

The composition of the present invention may comprise at least one additional skin care active, useful for regulating and/or improving the condition of mammalian skin. Classes of suitable skin care actives include, but are not limited to vitamins, peptides and peptide derivatives, sugar amines, sunscreens, oil control agents, particulates, flavonoid compounds, hair growth regulators, antioxidants and/or anti-oxidant precursors, preservatives, phytosterols, protease inhibitors, tyrosinase inhibitors, anti-inflammatory agents, and mixtures thereof. It should be noted, however, that many skin care actives may provide more than one benefit, or operate via more than one mode of action. Therefore, classifications herein are made for the sake of convenience and are not intended to limit the active to that particular application or applications listed.

A. Vitamins

The compositions of the present invention may comprise from about 0.0001% to about 50%, alternatively from about 0.001% to about 10%, alternatively from about 0.01% to about 5%, and alternatively from about 0.1% to about 1%, of one or more vitamins. Herein, "vitamins" means vitamins, pro-vitamins, and their salts, isomers and derivatives. Non-limiting examples of suitable vitamins include: vitamin B compounds (including B1 compounds, B2 compounds, B3 compounds such as niacinamide, niacinnicotinic acid, tocopheryl nicotinate, C1-C18 nicotinic acid esters, and nicotinyl alcohol; B5 compounds, such as panthenol or "pro-B5", pantothenic acid, pantothenyl; B6 compounds, such as pyroxidine, pyridoxal, pyridoxamine; carnitine, thiamine, riboflavin); vitamin A compounds, and all natural and/or synthetic analogs of Vitamin A, including retinoid compounds such as retinol, retinyl acetate, retinyl palmitate, retinoic acid, retinaldehyde, retinyl propionate; carotenoids (pro-vitamin A); vitamin D compounds; vitamin K compounds; vitamin E compounds, or tocopherol, including tocopherol sorbate, tocopherol acetate, other esters of tocopherol and tocopheryl compounds; vitamin C compounds, including ascorbate, ascorbyl esters of fatty acids, and ascorbic acid derivatives, for example, ascorbyl phosphates such as magnesium ascorbyl phosphate and sodium ascorbyl phosphate, ascorbyl glucoside, and ascorbyl sorbate; and vitamin F compounds, such as saturated and/or unsaturated fatty acids. In one embodiment, the composition comprises a vitamin selected from the group consisting of vitamin B compounds, vitamin C compounds, vitamin E compounds and mixtures thereof. Alternatively, the vitamin is selected from the group consisting of niacinamide, tocopheryl nicotinate, pyroxidine, panthenol, vitamin E, vitamin E acetate, ascorbyl phosphates, ascorbyl glucoside, and mixtures thereof.

B. Peptides and Peptide Derivatives

The compositions of the present invention may comprise one or more peptides. Herein, "peptide" refers to peptides containing ten or fewer amino acids, their derivatives, isomers, and complexes with other species such as metal ions (for example, copper, zinc, manganese, and magnesium). As used herein, peptide refers to both naturally occurring and synthesized peptides. In one embodiment, the peptides are di-, tri-, tetra-, penta-, and hexa-peptides, their salts, isomers, derivatives, and mixtures thereof. Examples of useful peptide derivatives include, but are not limited to, peptides derived from soy proteins, carnosine (beta-alanine-histidine), palmitoyl-lysine-threonine (pal-KT) and palmitoyl-lysine-threonine-threonine-lysine-serine (pal-KTTKS, available in a composition known as MATRIXYL®), palmitoyl-glycine-glutamine-proline-arginine (pal-GQPR, available in a composition known as RIGIN®), these three being available from Sederma, France, acetyl-glutamate-glutamate-methionine-glutamine-arginine-arginine (Ac-EEMQRR: Argireline®), and Cu-histidine-glycine-glycine (Cu-HGG, also known as IAMIN®).

The compositions may comprise from about $1 \times 10^{-7}$% to about 20%, alternatively from about $1 \times 10^{-6}$% to about 10%, and alternatively from about $1 \times 10^{-5}$% to about 5% of the peptide.

C. Sugar Amines

The compositions of the present invention may comprise a sugar amine, also known as amino sugars, and their salts, isomers, tautomers and derivatives. Sugar amines can be synthetic or natural in origin and can be used as pure compounds or as mixtures of compounds (e.g., extracts from natural sources or mixtures of synthetic materials). For example, glucosamine is generally found in many shellfish and can also be derived from fungal sources. Sugar amine compounds useful in the present invention include, for example, N-acetyl-glucosamine, and also those described in PCT Publication WO 02/076423 and U.S. Pat. No. 6,159,485, issued to Yu, et al. In one embodiment, the composition comprises from about 0.01% to about 15%, alternatively from about 0.1% to about 10%, and alternatively from about 0.5% to about 5%, of the sugar amine.

D. Sunscreens

The compositions of the subject invention may comprise one or more sunscreen actives (or sunscreen agents) and/or ultraviolet light absorbers. Herein, "sunscreen active" includes both sunscreen agents and physical sunblocks. Sunscreen actives and ultraviolet light absorbers may be organic or inorganic. Examples of suitable sunscreen actives and ultraviolet light absorbers are disclosed in The Cosmetic, Toiletry, and Fragrance Association's *The International Cosmetic Ingredient Dictionary and Handbook*, $10^{th}$ Ed., Gottschalck, T. E. and McEwen, Jr., Eds. (2004), p. 2267 and pp. 2292-93. Particularly suitable sunscreen actives include benzophenone, benzophenone-1, benzophenone-2, benzophenone-3, benzophenone-4, benzophenone-5, benzophenone-6, benzophenone-7, benzophenone-8, benzophenone-9, benzophenone-10, benzophenone-11, benzophenone-12, benzotriazolyl dodecyl p-cresol, 3-benzylidene camphor, benzylidene camphor sulfonic acid, benzyl salicylate, bis-ethylhexyloxyphenol methoxyphenyl triazine, bornelone, bumetrizole, butyl methoxydibenzoyl-methane, butyl PABA (p-aminobenzoic acid), cinnamidopropyl-trimonium chloride, cinoxate, dea-methoxycinnamate, dibenzoxazoyl naphthalene, di-t-butyl hydroxy-benzylidene camphor, diethylamino hydroxy-benzoyl hexyl benzoate, diethylhexyl butamido triazone, diethylhexyl 2,6-naphthalate, diisopropyl ethyl cinnamate, diisopropyl methyl cinnamate, di-methoxy-cinnamido-propyl ethyldimonium chloride ether, dimethyl PABA ethyl cetearyldimonium tosylate, dimorpholino-pyridazinone, dimorpholino-pyridazinone, disodium bisethylphenyl triaminotriazine stilbenedisulfonate, disodium distyrylbiphenyl disulfonate, disodium phenyl dibenzimidazole tetrasulfonate, drometrizole, drometrizole trisiloxane, ethyl dihydroxypropyl PABA, ethyl diisopropyl-cinnamate, ethylhexyl bis-isopentylbenzoxazolylphenyl melamine, ethyl dimethoxybenz-ylidene dioxoimidazolidine propionate, ethylhexyl dimethyl PABA, ethylhexyl methoxy-cinnamate, ethylhexyl methoxydibenzoyl-methane, ethylhexyl salicylate, ethylhexyl triazone, ethyl methoxycinnamate, ethyl PABA, ethyl urocanate, etocrylene, 4-(2-beta-glucopyrano-siloxy)propoxy-2-hydroxybenzophenone, glyceryl ethylhexanoate dimethoxycinnamate, glyceryl PABA, glycol salicylate, hexanediol disalicylate, homosalate, isoamyl cinnamate, isoamyl p-methoxycinnamate, isopentyl trimethoxycinnamate trisiloxane, isopropylbenzyl salicylate, isopropyl dibenzoylmethane, isopropyl methoxy-cinnamate, kaempferia galanga root extract, menthyl anthranilate, menthyl salicylate, methoxycinnamido-propyl hydroxysultaine, methoxycinnamido-propyl laurdimonium tosylate, 4-methylbenzylidene camphor, methylene bis-benzotriazolyl tetramethylbutyl-phenol, octocrylene, octrizole, PABA, PEG-25 PABA, phenylbenzimidazole sulfonic acid, polyacrylamidomethyl benzylidene camphor, polyamide-2, polyquaternium-59, polysilicone-15, potassium methoxycinnamate, potassium phenyl-benzimidazole sulfonate, red petrolatum, sodium benzotriazoyl butylphenol sulfonate, sodium phenylbenz-imidazole sulfonate, sodium urocanate, TEA-phenylbenzimidazole sulfonate, TEA-salicylate, terephthalylidene dicamphor sulfonic acid, tetrabutyl phenyl hydroxybenzoate, titanium dioxide, urocanic acid, zinc cerium oxide, zinc oxide, and mixtures thereof. In one embodiment, the composition comprises from about 1% to about 20%, and alternatively from about 2% to about 10% by weight of the composition, of the sunscreen active and/of ultraviolet light absorber. Exact amounts will vary depending upon the chosen sunscreen active and/or ultraviolet light absorber and the desired Sun Protection Factor (SPF), and are within the knowledge and judgment of one of skill in the art.

E. Oil Control Agents

The compositions of the present invention may comprise one or more compounds useful for regulating the production of skin oil, or sebum, and for improving the appearance of oily skin. Examples of suitable oil control agents include salicylic acid, dehydroacetic acid, benzoyl peroxide, vitamin B3 compounds (for example, niacinamide or tocopheryl nicotinate), their isomers, esters, salts and derivatives, and mixtures thereof. The compositions may comprise from about 0.0001% to about 15%, alternatively from about 0.01% to about 10%, alternatively from about 0.1% to about 5%, and alternatively from about 0.2% to about 2%, of an oil control agent.

F. Particulates

The compositions of the present invention may comprise one or more particulate materials. Nonlimiting examples of particulate materials useful in the present invention include colored and uncolored pigments, interference pigments (non-limiting examples include mica, layered with about 50-300 nm films of $TiO_2$, $Fe_2O_3$ silica, tin oxide, $Cr_2O_3$, and mixtures thereof; spherical $TiO_2$ particles having a size of from about 100 to about 300 nanometers; or alternatively, spherical $TiO_2$ particles having a size of from about 1 to about 30 micrometers; and mixtures thereof), inorganic powders (for example, iron oxides, zinc oxides, ferric ammonium ferrocyanide, manganese violet, ultramarine blue, and chrome oxide), organic powders (for example, phthalocyanine blue and green pigment), composite powders, optical brightener particles, and combinations thereof. These particulates can, for instance, be platelet shaped, spherical, elongated or needle-shaped, or irregularly shaped; surface coated or uncoated; porous or non-porous; charged or uncharged; and can be added to the current compositions as a powder or as a pre-dispersion.

In one embodiment, the compositions may comprise from about 0.01% to about 20%, alternatively from about 0.05% to about 10%, alternatively from about 0.1% to about 5%, of particulate materials.

G. Flavonoids

The compositions of the present invention may comprise a flavonoid. The flavonoid can be synthetic materials or obtained as extracts from natural sources, which also further may be derivatized. Examples of classes of suitable flavonoids are disclosed in U.S. Pat. No. 6,235,773, issued to Bissett, and include, but are not limited to, unsubstituted flavanones, methoxy flavanones, unsubstituted chalcones, and mixtures thereof. In one embodiment, the flavonoids are unsubstituted flavanones, unsubstituted chalcone (especially the trans-isomer), their glucosyl derivatives, and mixtures thereof. Other examples of suitable flavonoids include flavanones such as hesperidin compounds (e.g., glucosyl hesperidin), isoflavones such as soy isoflavones, including but not limited to genistein, daidzein, quercetin, and equol, their glucosyl derivatives, 2',4-dihydroxy chalcone, and mixtures thereof.

The compositions of the present invention may comprise from about 0.01% to about 20%, alternatively from about 0.1% to about 10%, and alternatively from about 0.5% to about 5% of flavonoids.

H. Hair Growth Regulators

The compositions of the present invention may comprise compounds useful for regulating hair growth. Suitable hair growth regulators include, but are not limited to, hexamidine, butylated hydroxytoluene (BHT), hexanediol, panthenol and pantothenic acid derivates, their isomers, salts and derivatives, and mixtures thereof. The compositions of the present invention may comprise from about 0.0001% to about 20%, alternatively from about 0.001% to about 10%, alternatively from about 0.01% to about 5%, and alternatively from about 0.1% to about 2% of hair growth regulators.

I. Other Skin Care Actives

The compositions of the present invention further may comprise non-vitamin antioxidants and radical scavengers, minerals, preservatives, phytosterols and/or plant hormones, protease inhibitors, tyrosinase inhibitors, anti-inflammatory agents and N-acyl amino acid compounds.

Suitable non-vitamin antioxidants and radical scavengers include, but are not limited to, BHT (butylated hydroxy toluene), L-ergothioneine (available as THIOTANE™); tetrahydrocurcumin, cetyl pyridinium chloride, camosine, diethylhexyl syrinylidene malonate (available as OXYNEX™), hexadec-8-ene-1,16-dicarboxylic acid (octadecene dioic acid; ARLATONE™ Dioic DCA from Uniqema), ubiquinone (co-enzyme Q10), tea extracts including green tea extract, yeast extracts (e.g., Pitera®), yeast culture fluid, and combinations thereof.

Suitable minerals include zinc, manganese, magnesium, copper, iron, selenium and other mineral supplements. "Mineral" is understood to include minerals in various oxidation states, mineral complexes, salts, derivatives, and combinations thereof.

Suitable examples of plant sterols (phytosterols) and/or plant hormones include, but are not limited to, sitosterol, stigmasterol, campesterol, brassicasterol, kinetin, zeatin, and mixtures thereof.

Suitable protease inhibitors include, but are not limited to, hexamidine, vanillin acetate, menthyl anthranilate, soybean trypsin inhibitor, Bowman-Birk inhibitor, and mixtures thereof.

Suitable tyrosinase inhibitors include, but are not limited to, sinablanca (mustard seed extract), tetrahydrocurcumin, cetyl pyridinium chloride, and mixtures thereof.

Suitable anti-inflammatory agents include, but are not limited to, glycyrrhizic acid (also known as glycyrrhizin, glycyrrhixinic acid, and glycyrrhetinic acid glycoside), glycyrrhetenic acid, other licorice extracts, and combinations thereof.

Suitable N-acyl amino acid compounds include, but are not limited to, N-acyl phenylalanine, N-acyl tyrosine, their isomers, including their D and L isomers, salts, derivatives, and mixtures thereof. An example of a suitable N-acyl amino acid is N-undecylenoyl-L-phenylalanine is commercially available under the tradename SEPIWHITE® from Seppic (France).

Other useful skin care actives include moisturizing and/or conditioning agents, such as glycerol, petrolatum, caffeine, and urea; yeast extracts (for example, Pitera™); dehydroepiandrosterone (DHEA), its analogs and derivatives; exfoliating agents, including alpha- and beta-hydroxyacids, alpha-keto acids, glycolic acid and octanoyl salicylate; antimicrobial agents; antidandruff agents such as piroctone olamine, 3,4,4'-trichlorocarbanilide (trichlosan), triclocarban and zinc pyrithione; dimethyl aminoethanol (DMAE); creatine; skin lightening agents such as kojic acid, mulberry extract, hydroquinone, arbutin, and deoxy-arbutin; (sunless) tanning agents, such as dihydroxy acetone (DHA); plant-derived materials such as resveratrol; isomers, salts, and derivatives of any of the foregoing; and mixtures thereof.

Dermatologically Acceptable Carrier

The compositions of the present invention comprise a dermatologically acceptable carrier for the skin care actives materials. The compositions may comprise from about 50% to about 99.99%, alternatively from about 60% to about 99.9%, alternatively from about 70% to about 98%, and alternatively from about 80% to about 95% of the composition.

The carrier can be a wide variety of types, non-limiting examples of which include solutions, dispersions, emulsions and combinations thereof. Herein, "emulsions" generally contain an aqueous phase and an oil phase. The oils may be derived from animals, plants, or petroleum, may be natural or synthetic, and may include silicone oils. Emulsion carriers include, but are not limited to oil-in-water, water-in-oil and water-in-oil-in-water emulsions. In one embodiment, the carrier comprises an oil-in-water emulsion, a water-in-oil emulsion a silicone-in-water emulsion, and/or a water-in-silicone emulsion. The emulsions may comprise from about 0.01% to about 10%, and alternatively from about 0.1% to about 5%, of a nonionic, anionic or cationic emulsifier, and combinations thereof. Suitable emulsifiers are disclosed in, for example, U.S. Pat. No. 3,755,560, U.S. Pat. No. 4,421,769, and *McCutcheon's Detergents and Emulsifiers*, North American Edition, pages 317-324 (1986).

The carrier further may comprise a conditioning agent and/or a thickening agent. Suitable conditioning agents include a humectant, moisturizer, and/or skin conditioner. The composition may comprise from about 0.01% to about 20%, alternatively from about 0.1% to about 10%, and alternatively from about 0.5% to about 7%, of a conditioning agent. In one embodiment, the conditioning agent is selected from urea, guanidine, sucrose polyester, panthenol, dexpanthenol, allantoin, glycerol, and mixtures thereof.

The compositions of the present invention may comprise from about 0.05% to about 5%, alternatively from about 0.1% to about 4%, and alternatively from about 0.25% to about 3%, of a thickening agent. Suitable classes of thickening agents include, but are not limited to carboxylic acid polymers, crosslinked polyacrylate polymers, polyacrylamide polymers, polysaccharides, gums and mixtures thereof. Non-limiting examples of suitable thickening agents are described in the *CTFA International Cosmetic Ingredient Dictionary*, 10th Ed. (2004), pp. 2294-96.

The composition further may comprise from about 0.1% to about 20%, alternatively from about 1% to about 10%, and alternatively from about 5% to about 7% of dipropylene glycol monocaprylate, isopropyl lauroyl sarcosinate, and mixtures thereof, suitable for use with oil soluble actives. Dipropylene glycol monocaprylate is commercially available as Caproyl™ 90 (Gattefosse, Gennevilliers, France). Isopropyl lauroyl sarcosinate is commercially available as Eldew™, which can be purchased from Ajinomoto U.S.A., Paramus, N.J. Non-limiting examples of oil-soluble actives suitable for use with dipropylene glycol monocaprylate and/or isopropyl lauroyl sarcosinate include, but are not limited to, tetrahydrocurcumin, tetrahydrocurmin diacetate, glycyrrhizic acid, glycyrrhetinic acid, lauryl p-cresol ketoxime, bis-abolol and ginger extract, alpha-linoleic acid, oil soluble vitamin C, carnosic acid, ursolic acid, proanthocyanidins, green tea polyphenols, oleuropein, xymenynic acid, ethyl p-methoxycinnamate, and lupeol hemisuccinate.

Optional Components

The compositions of the present invention may contain a variety of other ingredients that are conventionally used in given product types provided that they do not unacceptably alter the benefits of the invention.

The optional components, when incorporated into the composition, should be suitable for use in contact with human keratinous tissue without undue toxicity, incompatibility, instability, allergic response, and the like within the scope of sound judgment. The *CTFA Cosmetic Ingredient Handbook*, Second Edition (1992) describes a wide variety of nonlimiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, anti-caking agents, antifoaming agents, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, and thickeners.

II. Methods for Regulating Keratinous Tissue Condition

The present invention describes one or more methods of regulating the condition of mammalian skin and/or of providing a benefit to keratinous tissue. The method may comprise the step of topically applying to mammalian skin in need of regulation a personal care composition of the present invention. In one embodiment, the benefit is selected from the group consisting of reducing the appearance of wrinkles, deep lines, fine lines, crevices, bumps, large pores; increasing the convolution of the dermal-epidermal border; skin lightening; increasing elasticity, decreasing sagging, reducing cellulite; reducing the appearance of under-eye circles, reducing the appearance of discoloration, reducing hyperpigmentation, increasing skin luminosity, and combinations thereof. Alternatively, the benefit is selected from the group consisting of reducing hyperpigmentation, skin lightening, and combinations thereof. In one embodiment, the method comprises the step of selectively applying the composition to an area of skin in need of a benefit, where "selectively" is understood to mean that the composition is applied primarily to the area of skin in need of treatment, for example an age spot, and little or no composition is applied to the surrounding keratinous tissue that does not appear to be in need of treatment.

The composition may be applied by a variety of means, including by rubbing, wiping or dabbing with hands or fingers, or by means of an implement and/or delivery enhancement device. Non-limiting examples of implements include a sponge or sponge-tipped applicator, a swab (for example, a cotton-tipped swab), a pen optionally comprising a foam or sponge applicator, a brush, a wipe, and combinations thereof. Non-limiting examples of delivery enhancement devices include cloths, masks, substrates, gels (including pre-formed gels), temperature change elements, and combinations thereof. The composition may be pre-applied to the applicator, and for example delivered to the user pre-packaged as such, or the user may be instructed to apply the composition to the applicator prior to use. Alternatively, the composition may be stored in an implement, for example, in a cotton-tipped swab. The implement may comprise a separate storage area for the composition, and composition may be transferred to the applicator directly from the storage area, for example, by squeezing and/or breaking or by other suitable means. The composition may be applied to the keratinous tissue by contacting the applicator and composition to the skin. Contact may include, for example, light pressure, dabbing, rubbing, wiping, or any other suitable means. When targeted application is desired, the composition may be applied to the desired area of keratinous tissue by means of a suitable applicator.

The amount of the composition applied, the frequency of application and the period of use will vary widely depending upon the level of components of a given composition and the level of regulation desired. Quantities of the present composition typically applied per $cm^2$ of skin are from about 0.1 $mg/cm^2$ to about 20 $mg/cm^2$. Alternatively, a suitable application amount is about 0.5 $mg/cm^2$ to about 10 $mg/cm^2$. In one embodiment, the compositions are applied at least once daily, where "daily" and "days" mean a 24-hour period. For example, the compositions may be applied daily for 30 consecutive days, alternatively for 14 consecutive days, alternatively for 7 consecutive days and alternatively for 2 consecutive days.

The method may comprise the step of inducing a temperature change in the composition and/or in the keratinous tissue either simultaneously or sequentially with the step of applying the composition. The method further may comprise additional steps which form part of a treatment or application regimen, including the steps of applying at least one additional composition, ingesting one or more dietary supplements, cleansing, etc.

The present invention also contemplates the delivery of energy, via a delivery enhancement device, to keratinous tissue, either simultaneously and/or sequentially (e.g., within 10 minutes) with application of the topical compositions. The energy delivery device may deliver energy in a variety of forms, including but not limited to energy in the form of light, heat, sound (including ultrasonic energy), magnetic energy, electromagnetic energy (including radiofrequency waves and microwaves), mechanical energy (exfoliating or microdermabrasion device), and combinations thereof. In one embodiment, the energy is selected from the group consisting of light energy, heat energy, ultrasonic energy, magnetic energy, electromagnetic energy, mechanical energy, and combinations thereof. The delivery of energy may be continuous, pulsed, modulated, non-modulated, and combinations thereof. In one embodiment, the energy delivery device is hand-held. Alternatively, the energy delivery device is cordless.

The energy may be applied by holding a device within a single area of keratinous tissue, and subsequently moving the device to another area of tissue (or "stamping"). Alternatively, the energy may be applied as the device is continuously moved, or scanned, across the surface of the tissue. The device may be held in substantially continuous contact with the surface of the keratinous tissue, as with laser devices, or may be held at a short distance from the keratinous tissue with the energy directed toward the surface, as with flash lamps.

A temperature change may be simultaneously induced in the keratinous tissue or alternatively, in a compound applied to the surface of the tissue. This temperature change is in addition to any temperature change induced by the delivered energy itself. For example, the keratinous tissue may be slightly warmed prior to delivery of energy, or alternatively, the keratinous tissue may be cooled after delivery of energy.

III. Kit

The present invention further provides a kit comprising at least one composition described herein. The kit may comprise an outer packaging unit, which in turn may comprise one or more inner packaging units. The inner packaging units may be suitable for a single application, or "unit dose." The inner and outer packaging units may be of any type suitable for containing, presenting and/or reasonably protecting from damage the contents of the kit. The kit further may comprise an implement, which may be suitable for targeted delivery of the composition to a desired area of keratinous tissue. The composition may be packaged separately from the implement, or may be contained within the implement. The kit further may comprise a plurality of components, including but not limited to, one or more additional compositions, one or more orally ingestible dietary supplements, an implement, a delivery enhancement device, an energy delivery device, a temperature change element, instructions for use of the implement and/or device, instructions for complying with suitable application regimens, instructions for targeted delivery, a substrate, and combinations thereof.

When an implement such as a pen is included, a non-limiting example of which is SHO127F2 applicator from Shya Hsin™, one example of suitable instructions includes the following. Cleanse skin thoroughly before applying. Apply a thin layer of the product on the most visible dark spots, twice daily. To use: Turn the mechanism at the base of the pen until a drop of product appears at the end of the tip. Apply the concentrate on the most visible facial age spots, lightly massage product in by using the tip of the applicator to help penetration. If desired, you may follow up with your moisturizer or foundation makeup. Sun exposure should be limited by using a sunscreen agent, a sun blocking agent, or protective clothing.

When an implement such as a swab is included, a non-limiting example of which is an XPress Tip™ from Swab-Plus™, one example of suitable instructions includes the following. Directions: Cleanse skin thoroughly before applying. Apply a thin layer of the product on the most visible dark spots, twice daily. To use: Hold swab with soft tip pointing up, slowly push the upper tube down into the lower tube. Treatment product will flow up into the soft tip, continue to push product until desired amount of product is visible at the swab tip. Apply the concentrate on the most visible facial age spots, lightly massage product in by using the tip of the applicator to help penetration. If desired, you may follow up with your moisturizer or foundation makeup. Sun exposure should be limited by using a sunscreen agent, a sun blocking agent, or protective clothing. Dispose of swab after use.

IV. Article of Commerce

The present invention also provides articles of commerce comprising at least one personal care composition described herein, and communication pertaining to the personal care composition comprises indicia and/or an image which communicates to a consumer that the personal care composition can be used in conjunction with an implement and/or energy delivery device for regulating the condition of and/or providing a benefit to mammalian keratinous tissue. The communication may comprise images comparing the appearance of a person prior to use of the composition to the appearance of the same person after use of the composition. In one embodiment, the benefit is selected from the group consisting of skin lightening, reducing hyperpigmentation, and combinations thereof.

V. Method of Marketing

The present invention also provides methods of marketing personal care compositions for preventing, retarding, and/or treating uneven skin tone. One preferred method of marketing such compositions includes making available to a consumer a personal care composition described herein and communicating to the consumer that the topical application of the personal care composition may improve the consumer's skin color. The manner in which the communication is conveyed to the consumer is non-limiting. By way of example only, the communication can be effected by known advertisement techniques, such as, television, internet and magazine advertisements. The communication may be a point-of-sale technique, such as, for example, a shelf and/or floor affixed communication. Additionally or alternatively, he communication may take the form of indicia (text, symbols, colors, shades, figures, and the like) disposed in and/or on packaging of the personal care compositions.

Methods of conducting business are also contemplated by the present invention. One preferred method includes the step of communicating to a consumer a comparison between a first personal care composition comprising an active discussed herein and a second personal care composition that does not include the noted active. The comparison may relate to skin tone, skin lightening, skin whitening, pigmentation, among other parameters associated with regulating mammalian keratinous tissue conditions.

EXAMPLES

The following are non-limiting examples of the compositions of the present invention, and are prepared by conventional means as would be understood by one of skill in the art. The examples are given solely for the purpose of illustration and are not to be construed as limitations of the present invention, as many variations thereof are possible without departing from the spirit and scope of the invention, which would be recognized by one of ordinary skill in the art.

| Component | A | B | C | D | E | F |
|---|---|---|---|---|---|---|
| Disodium EDTA | 0.100 | 0.100 | 0.100 | 0.100 | 0.100 | 0.100 |
| Extract | 1.000 | 0.010 | 0 | 0 | 10.000 | 5.000 |
| 2-hexyldecanol | 0 | 0 | 0.0100 | 2.000 | 1.000 | 10.000 |
| Niacinamide | 5.000 | 10.000 | 1.000 | 0.0100 | 5.000 | 0.100 |
| Isohexadecane | 3.000 | 3.000 | 3.000 | 3.000 | 3.000 | 3.000 |
| Isopropyl isostearate | 1.330 | 1.330 | 1.330 | 1.330 | 1.330 | 1.330 |
| Sucrose polycottonseedate | 0.670 | 0.670 | 0.670 | 0.670 | 0.670 | 0.670 |
| Polymethylsilsesquioxane | 0.250 | 0.250 | 0.250 | 0.250 | 0.250 | 0.250 |
| Cetearyl glucoside + cetearyl alcohol | 0.200 | 0.200 | 0.200 | 0.200 | 0.200 | 0.200 |
| Behenyl alcohol | 0.400 | 0.400 | 0.400 | 0.400 | 0.400 | 0.400 |
| Ethylparaben | 0.200 | 0.200 | 0.200 | 0.200 | 0.200 | 0.200 |
| Propylparaben | 0.100 | 0.100 | 0.100 | 0.100 | 0.100 | 0.100 |
| Cetyl alcohol | 0.320 | 0.320 | 0.320 | 0.320 | 0.320 | 0.320 |
| Stearyl alcohol | 0.480 | 0.480 | 0.480 | 0.480 | 0.480 | 0.480 |
| Tocopheryl acetate | 0.500 | 0.500 | 0.500 | 0.500 | 0.500 | 0.500 |
| PEG-100 stearate | 0.100 | 0.100 | 0.100 | 0.100 | 0.100 | 0.100 |
| Glycerin | 7.000 | 7.000 | 7.000 | 7.000 | 7.000 | 7.000 |
| Titanium dioxide | 0.604 | 0.604 | 0.604 | 0.604 | 0.604 | 0.604 |
| Polyacrylamide + C13-14 isoparaffin + laureth-7 | 2.000 | 2.000 | 2.000 | 2.000 | 2.000 | 2.000 |
| Panthenol | 1.000 | 1.000 | 1.000 | 1.000 | 1.000 | 1.000 |
| Benzyl alcohol | 0.400 | 0.400 | 0.400 | 0.400 | 0.400 | 0.400 |
| Dimethicone + dimethiconol | 2.000 | 2.000 | 2.000 | 2.000 | 2.000 | 2.000 |
| Water (to 100 g) | qs to 100 | qs to 100 | qs to 100 | qs to 100 | qs to 100 | qs to 100 |
| TOTAL | 100 | 100 | 100 | 100 | 100 | 100 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

Whereas particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating skin discoloration, comprising the step of selectively applying to an area of discolored skin in need of such treatment a personal care composition comprising:
    (1) an effective amount of 2-hexyldecanol, wherein the effective amount of 2-hexyldecanol inhibits the synthesis of melanin in the skin, wherein the effective amount of 2-hexyldecanol present in the composition is between 0.01% and 10%;
    (2) an effective amount of niacinamide; and
    (3) a dermatologically acceptable carrier.

2. The method of claim 1, wherein the composition is applied with an implement selected from the group consisting of a swab, a pen, and combinations thereof.

3. The method of claim 1, wherein said discolored skin in need of such treatment is selected from the group consisting of hyperpigmented skin, an age spot, a pigment spot, blotchy skin, skin with uneven skin tone, sallow skin, a freckle, skin with keratosis, abnormally differentiated skin, hyperkeratinized skin, and combinations thereof.

4. The method of claim 1, wherein said discolored skin in need of such treatment is hyperpigmented skin.

5. The method of claim 1, wherein said discolored skin in need of such treatment is an age spot.

6. The method of claim 1, wherein said discolored skin in need of such treatment is a pigment spot.

7. The method of claim 1, wherein said discolored skin in need of such treatment is blotchy skin.

8. The method of claim 1, wherein said discolored skin in need of such treatment is skin with uneven skin tone.

9. The method of claim 1, wherein said discolored skin in need of such treatment is sallow skin.

10. The method of claim 1, wherein said discolored skin in need of such treatment is a freckle.

11. The method of claim 1, wherein said discolored skin in need of such treatment is skin with keratosis.

12. The method of claim 1, wherein said discolored skin in need of such treatment is abnormally differentiated skin.

13. The method of claim 1, wherein said discolored skin in need of such treatment is hyperkeratinized skin.

14. The method of claim 1, wherein the effective amount of 2-hexyldecanol present in the composition is between 0.05% and 5%.

* * * * *